(12) United States Patent
Zhu et al.

(10) Patent No.: US 8,242,264 B2
(45) Date of Patent: Aug. 14, 2012

(54) PROCESS FOR PREPARING 4-ACETYL-2,3,4,5-TETRAHYDRO-BENZO[1,4]DIAZEPINE AND THE INTERMEDIATES THEREOF

(75) Inventors: Fuqiang Zhu, Shanghai (CN); Haihong Li, Shanghai (CN); Wenzhong Wang, Shanghai (CN); Hui Zhang, Shanghai (CN); Jingshan Shen, Shanghai (CN)

(73) Assignees: Topharman Shanghai Co., Ltd., Shanghai (CN); Weifang Tehua Chemical Co., Ltd., Shandong (CN)

( * ) Notice: Subject to any disclaimer, the term of this patent is extended or adjusted under 35 U.S.C. 154(b) by 294 days.

(21) Appl. No.: 12/601,962

(22) PCT Filed: May 22, 2008

(86) PCT No.: PCT/CN2008/001001
§ 371 (c)(1),
(2), (4) Date: May 18, 2010

(87) PCT Pub. No.: WO2008/145010
PCT Pub. Date: Dec. 4, 2008

(65) Prior Publication Data
US 2010/0256358 A1    Oct. 7, 2010

(30) Foreign Application Priority Data
May 25, 2007   (WO) ................ PCT/CN2007/070052

(51) Int. Cl.
C07D 243/14   (2006.01)
C07C 205/06   (2006.01)

(52) U.S. Cl. ........ 540/574; 564/219; 564/273; 564/384; 564/385

(58) Field of Classification Search ............... 540/574; 564/219, 273, 384, 385
See application file for complete search history.

(56) References Cited

FOREIGN PATENT DOCUMENTS
CN    1214685 A    4/1999
CN    1596114 A    3/2005

OTHER PUBLICATIONS

Saab, Annmarie L., et al. "Cycloalkyl[b][1,4]benzodiazepinoindoles are agonists at the human 5-HT2C receptor," *Bioorganic & Medicinal Chemistry Letters*, 2004, 14(10), 2603-2607.
International Search Report for PCT/CN2008/001001; Aug. 2008.

*Primary Examiner* — Brenda Coleman
(74) *Attorney, Agent, or Firm* — Baker & Hostetler LLP

(57) ABSTRACT

The present invention relates to a process for preparing 4-acetyl-2,3,4,5-tetrahydro-benzo[1,4]diazepine and the intermediates thereof. The present invention provides a compound represented by formula I and a compound represented by formula II, and processes for preparing 4-acetyl-2,3,4,5-tetrahydro-benzo[1,4]diazepine by using the compound represented by formula I, the compound represented by formula II and o-nitrobenzaldehyde. The invention has the advantages of the shorter synthesis steps, easily available raw materials and simple operation. Moreover, the process is economic and safe by avoiding the use of expensive and dangerous lithium aluminum hydride.

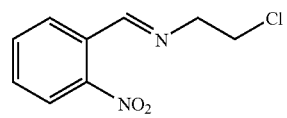

I

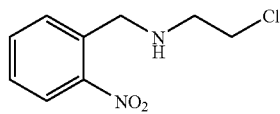

II

13 Claims, No Drawings

PROCESS FOR PREPARING 4-ACETYL-2,3,4,5-TETRAHYDRO-BENZO[1,4]DIAZEPINE AND THE INTERMEDIATES THEREOF

CROSS-REFERENCE TO RELATED APPLICATIONS

This is a national stage of International Application No. PCT/CN2008/001001, filed on May 22, 2008, the disclosure of which is hereby incorporated by reference in its entirety.

FIELD OF THE INVENTION

The present invention relates to a process for preparing 4-acetyl-2,3,4,5-tetrahydro-benzo[1,4]diazepine and the intermediates thereof. More specifically, it relates to the compounds represented by formula I, II and IV, the processes for preparing the same, and their uses in the preparation of 4-acetyl-2,3,4,5-tetrahydro-benzo[1,4]diazepine.

BACKGROUND OF THE INVENTION

4-Acetyl-2,3,4,5-4H-benzo[1,4]diazepine (represented by formula A) is a pharmaceutical intermediate with biological activity, and has been applied in the preparation of tranquilization, antibiotic and anticancer drugs (J. Med. Chem. 1999, 42, 5241; J. Med. Chem. 1996, 39, 3539; Bioorg. Med. Chem. Lett., 2004, 14, 2603).

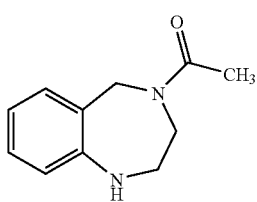

A

According to the literatures, in general, the compound represented by formula A is prepared by reducing 1,3,4-3H-benzo[1,4]diazepine-2,5-dione (represented by formula B) with LiAlH$_4$ to give a key intermediate represented by formula III, and then acetylating the compound represented by formula III, which is illustrated by reaction scheme 1. This process has disadvantages in that it needs high cost raw materials and is not suitable for a large-scale commercial production, because expensive LiAlH$_4$ was used in a very large amount in the reaction for preparing compound III from compound B, and anhydrous tetrahydrofuran which is difficult to be recovered was used as a solvent.

Reaction scheme 1

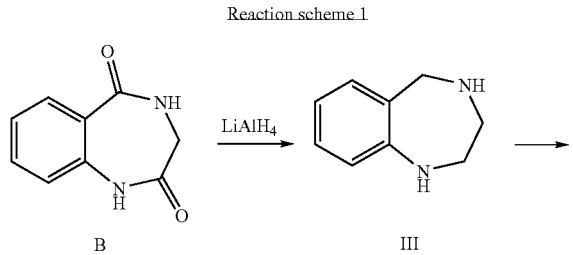

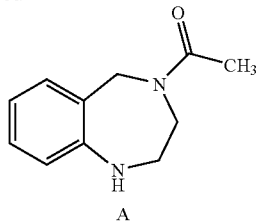

A

SUMMARY OF THE INVENTION

The inventors are directed to find a process for preparing 4-acetyl-2,3,4,5-4H-benzo[1,4]diazepine which is secure, simple, economic and suitable for large-scale commercial production, and thus the compounds represented by formula I, formula II and formula IV are invented and can be used to synthesize 4-acetyl-2,3,4,5-4H-benzo[1,4]diazepine in a facile and safe way.

Therefore, an object of the present invention is to provide the compounds represented by the formulae below, and another object of the present invention is to provide uses of these compounds for preparing 4-acetyl-2,3,4,5-4H-benzo[1, 4]diazepine, an important pharmaceutical intermediate.

Hereinafter, the present invention will be described in detail.

The present invention provides a compound represented by formula I:

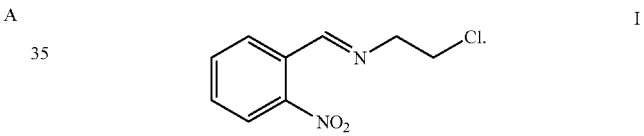

I

The present invention provides a process for preparing the compound represented by formula I, including condensing 2-nitrobenzaldehyde with 2-chloroethylamine hydrochloride in an organic solvent to yield the compound represented by formula I, as illustrated by reaction scheme 2:

Reaction scheme 2

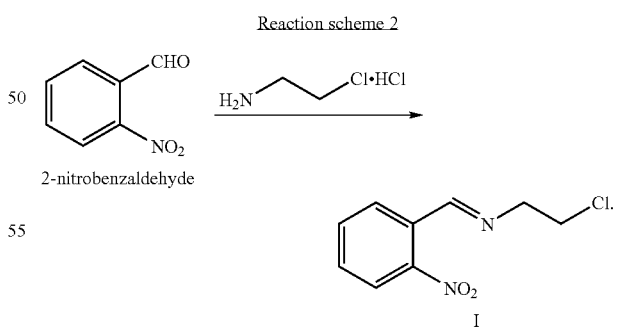

In the above condensation reaction, the organic solvent is one selected from the group consisting of methanol, ethanol, propanol, isopropanol, 1-butanol, 2-butanol, tert-butanol, 1-pentanol, 3-pentanol, ethyl acetate, ethylene glycol diethyl ether, ethylene glycol monomethyl ether, dichloromethane, 1,2-dichloroethane, toluene, xylene, DMF, DMSO, acetonitrile, tetrahydrofuran, dioxane and any mixture thereof.

The condensation reaction can be performed in the presence of water and a base selected from the group consisting of sodium methoxide, sodium ethoxide, sodium tert-butoxide, triethylamine, tri-n-butylamine, tripropylamine and pyridine.

The present invention provides a process for preparing a compound represented by formula II by using the compound represented by formula I,

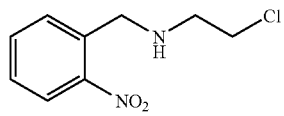

including:

reducing the compound represented by formula I in the presence of a reducing agent to give the compound represented by formula II, as illustrated by reaction scheme 3:

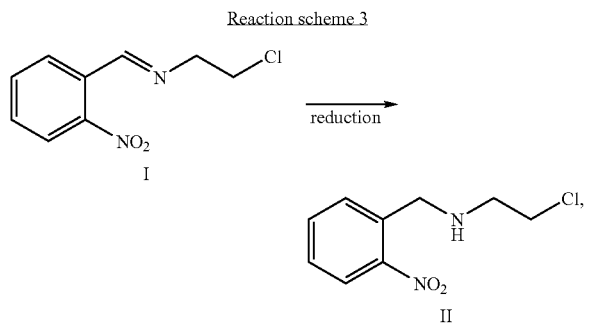

wherein the reducing agent is one selected from the group consisting of $NaBH_4$, $KBH_4$ and $LiBH_4$.

The present invention also provides a process for preparing a compound represented by formula A by using the compound represented by formula I, including:

reducing the nitro group of the compound represented by formula I and cyclizing the compound in the presence of a reducing agent selected from the group consisting of Fe powder, Zn powder and $SnCl_2$ in an organic solvent to give a compound represented by formula V;

reducing the double bond of the compound represented by formula V in the presence of a reducing agent selected from the group consisting of $NaBH_4$, $KBH_4$ and $LiBH_4$ to give a compound represented by formula III; and then acetylating the compound represented by formula III with an acetylating agent selected from the group consisting of $Ac_2O$ and acetyl chloride to give the compound represented by formula A;

which is illustrated by reaction scheme 4:

Reaction scheme 4

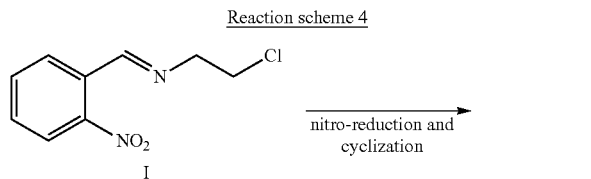

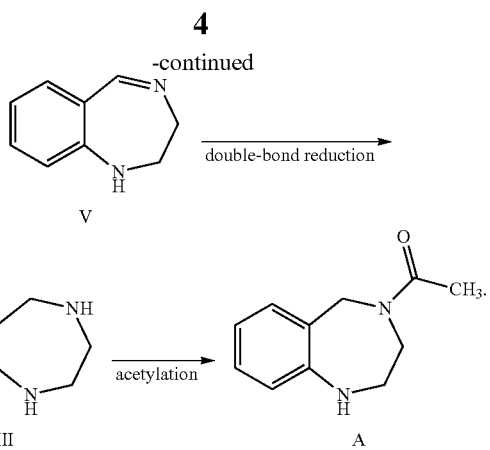

The present invention provides a compound represented by the following formula II or its hydrochloride salt:

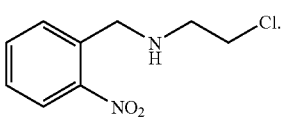

As mentioned above, the compound represented by formula II can be prepared by reducing the compound represented by formula I in the presence of a reducing agent. Its hydrochloride salt can be obtained by treating the compound represented by formula II with hydrochloride-ethanol.

The present invention provides a process for preparing a compound represented by formula A by using the compound represented by formula II,

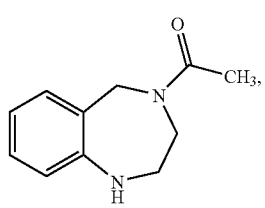

including:

acetylating the compound represented by formula II with an acetylating agent selected from the group consisting of $Ac_2O$ and acetyl chloride in an organic solvent to give a compound represented by formula IV, and then reducing and cyclizing the compound represented by formula IV in the presence of a reducing agent selected from the group consisting of Fe powder, Zn powder and $SnCl_2$ in an organic solvent to give the compound represented by formula A, which is illustrated by reaction scheme 5:

Reaction scheme 5

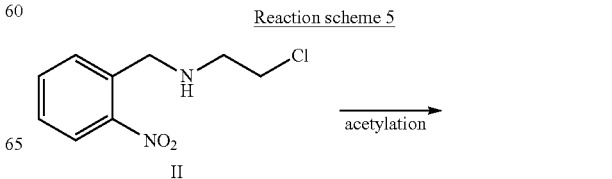

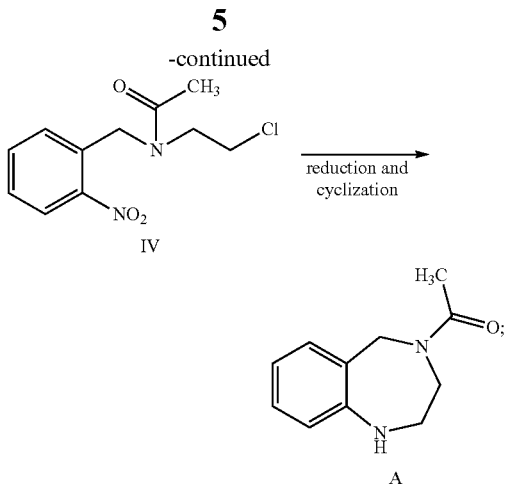

or reducing and cyclizing the compound represented by formula II in the presence of a reducing agent selected from the group consisting of Fe powder, Zn powder and SnCl₂ in an organic solvent to give the compound represented by formula III, and then acetylating the compound represented by formula III with an acetylating agent selected from the group consisting of Ac₂O and acetyl chloride to give the compound represented by formula A, which is illustrated by reaction scheme 6:

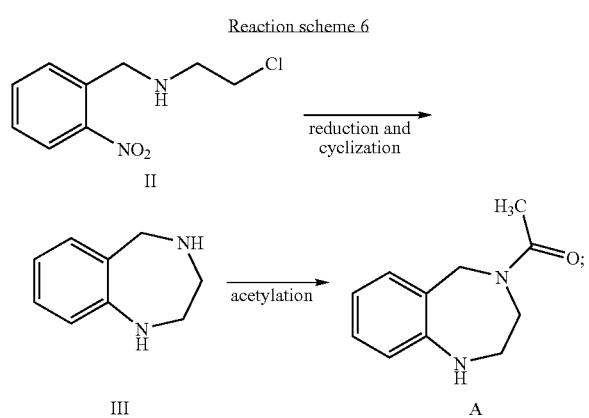

or reducing, cyclizing and acetylating simultaneously the compound represented by formula II in the presence of a reducing agent selected from the group consisting of Fe powder, Zn powder and SnCl₂ and an acetylating agent selected from the group consisting of Ac₂O and acetyl chloride in an organic solvent to give the compound represented by formula A, as illustrated by reaction scheme 7:

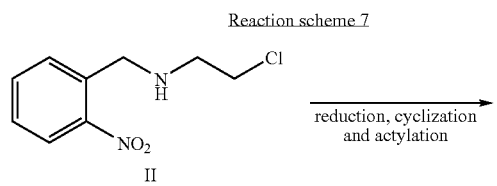

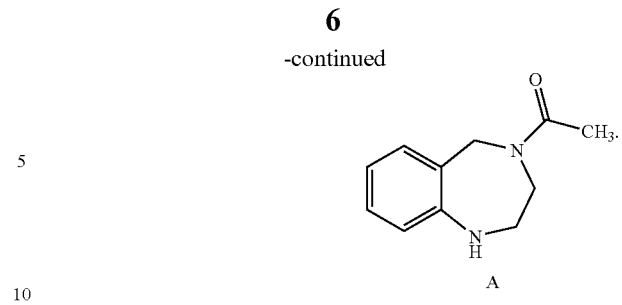

The present invention also provides a process for preparing the compound represented by formula A from 2-nitrobenzaldehyde, including: in an organic solvent, after condensing 2-nitrobenzaldehyde with 2-chloroethylamine hydrochloride, performing nitro-reduction and cyclization reaction in the presence of a reducing agent selected from the group consisting of Fe powder, Zn powder and SnCl₂, followed by a double bond-reduction in the presence of a reducing agent selected from the group consisting of NaBH₄, KBH₄ and LiBH₄ to give the compound represented by formula III; and then acetylating the compound represented by formula III with an acetylating agent to give the compound represented by formula A, which is illustrated in reaction scheme 8:

Reaction scheme 8

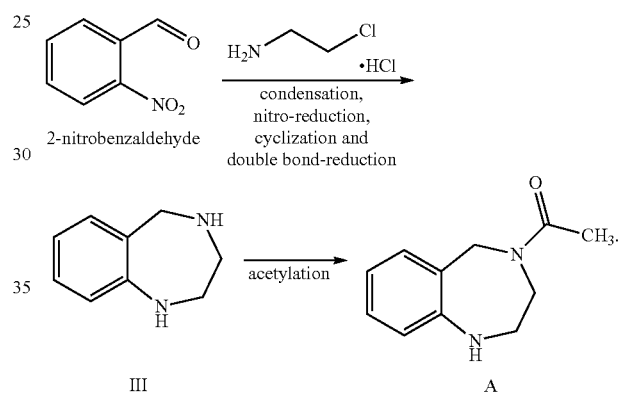

In the acetylating reactions according to the present invention, for example, the reaction for acetylating the compound represented by formula III to give the compound represented by formula A and the reaction for acetylating the compound represented by formula II to give the compound represented by formula IV, and so on, the acetylating reactions are performed preferably in the presence of a base selected from the group consisting of sodium methoxide, sodium ethoxide, sodium tert-butoxide, triethylamine, tri-n-butylamine, tripropylamine and pyridine.

In the present invention, the used organic solvent is one selected from the group consisting of methanol, ethanol, propanol, isopropanol, 1-butanol, 2-butanol, tert-butanol, 1-pentanol, 3-pentanol, ethyl acetate, ethylene glycol diethyl ether, ethylene glycol monomethyl ether, dichloromethane, 1,2-dichloroethane, toluene, xylene, DMF, DMSO, acetonitrile, tetrahydrofuran, dioxane and any mixture thereof.

The present invention also provides a compound represented by formula IV:

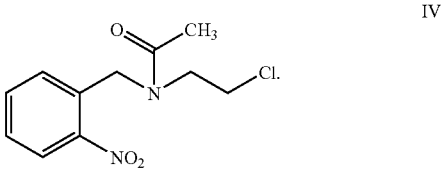

The advantageous technical effects of the present invention are as follows. The present invention provides a novel process for preparing 4-acetyl-2,3,4,5-4H-benzo[1,4]diazepine, which is simple and easy-operated with easily available raw materials. The process according to the present invention is also economic and safe for the sake of avoiding the use of the expensive and unsafe LiAlH$_4$.

DETAILED DESCRIPTION

Hereinafter, the technical solution of the present invention will be further illustrated by the Examples. The following examples are set forth to illustrate the invention more specifically, but are not to be construed to limit the technical solution of the present invention. All of the technical solutions of the present invention described above are those that can fulfill the aim of the present invention, that is, all of the reagents and temperatures used in the following examples can be interchanged with the corresponding reagents and temperatures described above to realize the objects of the present invention.

In the following examples, nuclear magnetic resonance (NMR) spectra were obtained on a Brucker AMX-400 NMR or Varian INVOA-600 NMR spectrometer with TMS as a IS, and the chemical shifts were reported in parts per million (ppm). Mass spectra were measured with a Finnigan MAT-95 or MAT-711 spectrometer. Silica gel with 200-300 mesh for column chromatography was purchased from Qingdao Ocean Chemical Co. Ltd. The silica gel plates for thin layer chromatography (TLC) were HSGF-254 preformed plates, which were commercially available from Yantai Huiyou Company, Yantai, China. The petroleum ether has a boiling point in the range of 60 to 90° C. The samples were monitored under UV-lamp and in iodine vapour. Unless stated otherwise in the examples, "concentrating" means that the solvents are distilled from the solution of the product by using a rotary evaporator, and "drying" indicates that the prepared compound is dried in a DHG-9240 thermostatic oven at 60° C.

EXAMPLE 1

Preparation of
2-chloro-N-(2-nitrobenzylidene)ethanamine
(Compound Represented by Formula I, Referred to as Compound I Hereinafter)

2-nitrobenzaldehyde (20 g, 0.13 mol), 2-chloroethylamine hydrochloride (15 g, 0.14 mol), pyridine (8 ml, 0.13 mol) and toluene (150 ml) were mixed together, and the mixture was heated to be refluxed. After stirred for 3 hours, the reaction mixture was concentrated to give compound I (yield: 95%). $^1$H NMR (300 MHz, CDCl$_3$): δ 3.85 (t, 2H, CH$_2$), 3.99 (t, 2H, CH$_2$), 7.60-8.02 (m, 4H, H on phenyl), 8.78 (s, 1H, CH).

EXAMPLE 2

Preparation of
2-chloro-N-(2-nitrobenzyl)ethanamine hydrochloride
(Compound Represented by Formula II, Referred to as Compound II Hereinafter)

2-nitrobenzaldehyde (20 g, 0.13 mol), 2-chloroethylamine hydrochloride (15 g, 0.14 mol), MeOH (150 ml) were mixed together, and the mixture was stirred for 3 hours at room temperature. KBH$_4$ (3.4 g, 0.06 mol) was added into the reaction mixture in 4 portions (interval time: 10 minutes), and the stirring continued for 5 hours at room temperature. After the evaporation of some MeOH, the reaction mixture was adjusted to a pH of 9 to 10 with NaHCO$_3$ saturated solution, and extracted with dichloromethane. The resulting organic phase was washed with saturated brine, dried with anhydrous Na$_2$SO$_4$, and concentrated to give compound II as a white solid, which was then treated with hydrochloride-EtOH to give its hydrochloride salt (yield: 90%). $^1$H NMR (300 MHz, DMSO): δ 3.45 (t, 2H, CH$_2$), 3.99 (t, 2H, CH$_2$), 4.51 (s, 2H, CH$_2$), 7.70-8.22 (m, 4H, H on phenyl).

EXAMPLE 3

Preparation of
2,3,4,5-tetrahydro-1H-benzo[e][1,4]diazepine
(Compound Represented by Formula III, Referred to as Compound III Hereinafter)

Compound I (20 g, 0.1 mol) was dissolved in ethanol (150 ml), and Fe powder (11 g) was fed into the reaction mixture in 3 portions (interval time: 30 minutes). After stirred for 3 hours at 40-45° C., the reaction mixture was cooled, filtered to remove the Fe powder and insoluble solid. The filtered solid was washed with ethanol (50 ml), and the combined organic filtrate was added with K$_2$CO$_3$ (69 g, 0.5 mol) under ice bath. After stirred for 30 minutes, the reaction mixture was treated with NaBH$_4$ g, 0.29 mol) in batches, stirred for another 30 minutes, filtered and concentrated. Dichloromethane (200 ml) and water (150 ml) were added into the resulting mixture, and the water phase was adjusted to a pH of 13 to 14 with NaOH (50% in water) and extracted with dichloromethane (150 ml×2). The combined organic phase was dried with anhydrous Na$_2$SO$_4$, concentrated to about 250 ml, and then treated with hydrochloride-isopropanol to give compound III in hydrochloride salt form (73 g, 65%). $^1$H NMR (300 MHz, CDCl$_3$): δ 3.06 (m, 4H, 2CH$_2$), 3.92 (s, 2H, CH$_2$), 6.76-7.26 (m, 4H, H on phenyl).

EXAMPLE 4

Preparation of
2,3,4,5-tetrahydro-1H-benzo[e][1,4]diazepine
(Compound III)

Compound II (21 g, 0.1 mol) was dissolved in ethanol (150 ml), and Fe powder (11 g) was fed into the reaction solution in 3 portions (interval time: 30 minutes). After stirred for 3 hours at 40-45° C., the reaction mixture was cooled and filtered to remove the Fe powder and insoluble solid. After concentrated, the filtrate was diluted with water (500 ml), and extracted with dichloromethane (3×50 ml). The water phase was adjusted to a pH of 9 to 10 with NaOH (1N) and extracted with dichloromethane again (3×100 ml). The combined organic phases were dried with anhydrous Na$_2$SO$_4$, filtered and concentrated to give compound III (yield: 70%).

EXAMPLE 5

Preparation of
2,3,4,5-tetrahydro-1H-benzo[e][1,4]diazepine
(Compound III) Hydrochloride 2-nitrobenzaldehyde (75.5 g, 0.5 mol), 2-chloroethylamine hydrochloride (58 g, 0.5 mol), pyridine (40.3 ml, 0.5 mol) and ethanol (453 ml) were mixed together, and the mixture was stirred for 4 hours at room temperature. water (45 ml) and Fe powder (84 g, 1.5 mol) were then added thereinto, and the reaction mixture was refluxed for 2 hours. After cooled, the mixture was filtered and the filtered solid was washed with ethanol (50 ml). After the addition of K$_2$CO$_3$ (69 g, 0.5 mol) under ice-bath, the combined filtrate was stirred for 30 minutes, and added by NaBH$_4$ (11 g, 0.29 mol). The stirring continued for another 30 minutes, and the reaction mixture was filtrated, concentrated, and added with dichloromethane (200 ml) and water (150 ml). The water phase was adjusted to a pH of 13 to 14 with NaOH (50% in water) and extracted with dichloromethane (150 ml×2). The combined organic phase was dried with anhydrous $Na_2SO_4$, concentrated to about 250 ml, and treated with hydrochloride-isopropanol to give the hydrochloride salt of compound III (66 g, yield: 60%).

EXAMPLE 6

Preparation of N-(2-chloroethyl)-N-(2-nitrobenzyl) acetamide (Compound Represented by Formula IV, Referred to as Compound IV Hereinafter)

Method 1: Under ice-bath cooling, compound II (21 g, 0.1 mol) was dissolved in dichloromethane (100 ml), and then added dropwise with acetyl chloride (10 ml). After the removal of the ice bath, the reaction mixture was stirred for 3 hours at room temperature, and poured into ice-water. The organic phase was separated, and concentrated to give compound IV (yield: 95%). $^1$H NMR (300 MHz, $CDCl_3$): δ 2.09 (s, 3H, $CH_3$), 3.70 (m, 4H, $2CH_2$), 4.97 (s, 2H, $CH_2$), 7.29-8.04 (m, 4H, H on phenyl).

Method 2: Under ice-bath cooling, compound II (21 g, 0.1 mol) was dissolved in dichloromethane (100 ml), $Et_3N$ (5 ml) was added thereinto, and then acetyl chloride (10 ml) was added dropwise. After the removal of the ice bath, the reaction mixture was stirred for 1.5 hours at room temperature, and poured into ice-water. The organic phase was separated, and concentrated to give compound IV (yield: 96%).

EXAMPLE 7

Preparation of the Compound Represented by Formula A (Referred to as Compound A Hereinafter)

Method 1: Under ice-bath cooling, compound III (14.8 g, 0.1 mol) was dissolved in dichloromethane (80 ml), $Et_3N$ (5 ml) was added thereinto, and then acetyl chloride (6 ml) was added dropwise. After the removal of the ice bath, the reaction mixture was stirred for 2 hours at room temperature, and poured into ice-water. The organic phase was separated, and concentrated to give a brown oily material, which was recrystallized in ethyl ether to give compound A (yield: 97%). $^1$H NMR (300 MHz, DMSO): δ 1.95 and 2.02 (s+s, 3H), 3.05 and 3.09 (m, 2H, $CH_2$), 3.60 (m, 2H, $CH_2$), 4.58 and 4.64 (s+s, 2H, $CH_2$), 7.1-7.3 (m, 4H, H on phenyl). Mp 83.4-84.4° C.; MS (EI) m/z: 190 ($M^+$).

Method 2: Under ice-bath, compound III (14.8 g, 0.1 mol) was dissolved in dichloromethane (80 ml), and acetyl chloride (6 ml) was added dropwise thereinto. After the addition was finished, the ice bath was removed and the reaction mixture was continually stirred at room temperature for 5 hours. Then, the mixture was poured into ice-water, and the organic phase was separated and concentrated to give a brown oily material, which was recrystallized in acetone to give compound A (yield 96%).

EXAMPLE 8

Preparation of Compound A

Method 1: At room temperature, compound II (21 g, 0.1 mol) was dissolved in dichloromethane (150 ml), $Et_3N$ (5 ml) and $Ac_2O$ (10 ml) were added thereinto, and then Fe powder (11 g) was added in 3 portions (interval time: 30 minutes). The reaction mixture was heated and stirred for 8 hours at 40-45° C. After cooled, the reaction mixture was filtered to remove the Fe powder and insoluble solid. The filtrate was concentrated and diluted with water (500 ml). The resulting water phase was extracted with dichloromethane (3×50 ml), adjusted to a pH of 12 with NaOH (1N) and extracted with dichloromethane again (3×100 ml). The combined organic phases was dried with anhydrous $Na_2SO_4$, and concentrated to give a brown oily material, which was recrystallized in ethyl ether to give compound A (yield: 65%).

Method 2: At room temperature, compound II (21 g, 0.1 mol) was dissolved in dichloromethane (150 ml), $Ac_2O$ (10 ml) was added thereinto, and then Fe powder (11 g) was added in 3 portions (interval time: 30 minutes). The reaction mixture was heated and stirred for 18 hours at 40-45° C. After cooled, the reaction mixture was filtered to remove the Fe powder and insoluble solid, and the filtrate was concentrated and diluted with water (500 ml). The resulting water phase was extracted with dichloromethane (3×50 ml), adjusted to a pH of 12 with NaOH (1N), and extracted with dichloromethane again (3×100 ml). The combined organic phase was dried with anhydrous $Na_2SO_4$, and concentrated to give a brown oily material, which was recrystallized in acetone to give compound A (yield: 45%).

EXAMPLE 9

Preparation of Compound A

At room temperature, compound IV (25.6 g, 0.1 mol) was dissolved in dichloromethane (200 ml) at room temperature, and Fe powder (11 g) was added thereinto in 3 portions (interval time: 30 minutes). The reaction mixture was heated and stirred for 5 hours at 40-45° C. After cooled, the reaction mixture was filtered to remove the Fe powder and insoluble solid, and the filtrate was concentrated and diluted with water (500 ml). The resulting water phase was extracted with dichloromethane (3×50 ml), adjusted to a pH of 12 with NaOH (1N), and extracted with dichloromethane again (3×100 ml). The combined organic phase was dried with anhydrous $Na_2SO_4$, and concentrated to give a brown oily material, which was recrystallized in acetone to give compound A (yield: 70%).

We claim:

1. A compound represented by formula I:

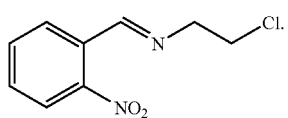

I

2. A process for preparing the compound represented by formula I according to claim 1, comprising condensing 2-nitrobenzaldehyde with 2-chloroethylamine hydrochloride in an organic solvent to yield the compound represented by formula I, as illustrated by reaction scheme 2:

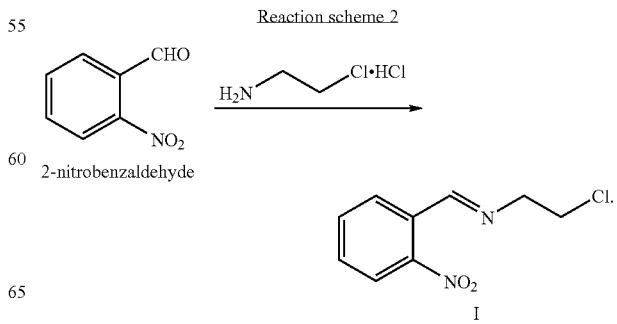

3. The process according to claim 2, wherein the organic solvent is one selected from the group consisting of methanol, ethanol, propanol, isopropanol, 1-butanol, 2-butanol, tert-butanol, 1-pentanol, 3-pentanol, ethyl acetate, ethylene glycol diethyl ether, ethylene glycol monomethyl ether, dichloromethane, 1,2-dichloroethane, toluene, xylene, DMF, DMSO, acetonitrile, tetrahydrofuran, dioxane and any mixture thereof.

4. The process according to claim 2, wherein the condensation is performed in the presence of a base selected from the group consisting of sodium methoxide, sodium ethoxide, sodium tert-butoxide, triethylamine, tri-n-butylamine, tripropylamine and pyridine.

5. A process for preparing a compound represented by formula II or its hydrochloride salt by using the compound represented by formula I according to claim 1,

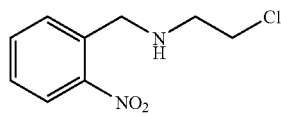

comprising:
reducing the compound represented by formula I in the presence of a reducing agent to give the compound represented by formula II, as illustrated by reaction scheme 3:

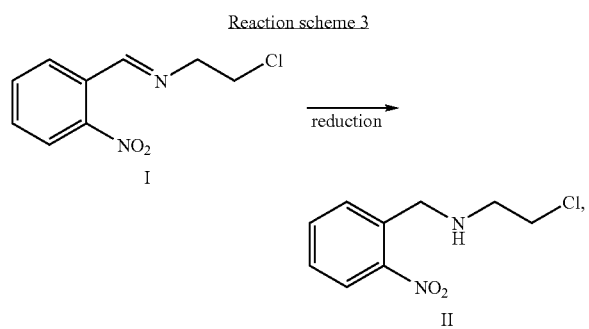

wherein the reducing agent is one selected from the group consisting of NaBH$_4$, KBH$_4$ and LiBH$_4$; and
treating the compound represented by formula II with hydrochloride-ethanol to give its hydrochloride salt.

6. A process for preparing a compound represented by formula A by using the compound represented by formula I according to claim 1,

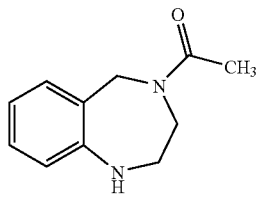

comprising:
reducing the nitro group of the compound represented by formula I and cyclizing the compound in the presence of a reducing agent selected from the group consisting of Fe powder, Zn powder and SnCl$_2$ in an organic solvent to give a compound represented by formula V;
reducing the double bond of the compound represented by formula V in the presence of a reducing agent selected from the group consisting of NaBH$_4$, KBH$_4$ and LiBH$_4$ to give a compound represented by formula III; and then acetylating the compound represented by formula III with an acetylating agent selected from the group consisting of Ac$_2$O and acetyl chloride to give the compound represented by formula A;
which is illustrated by reaction scheme 4:

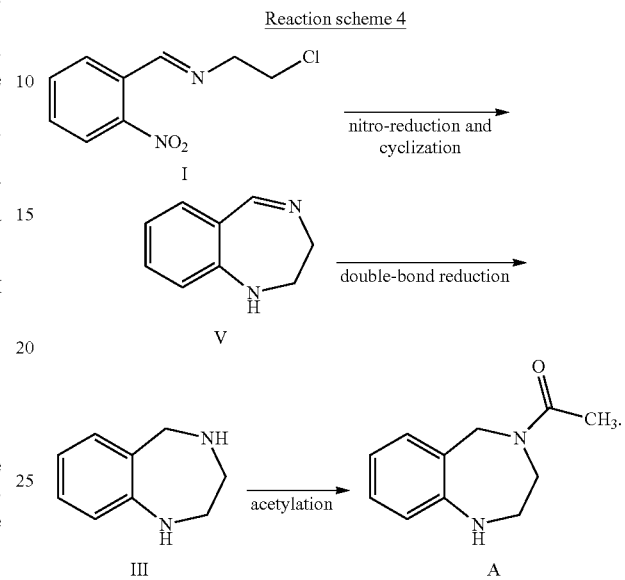

7. The process according to claim 6, wherein the acetylating reaction is performed in the presence of a base selected from the group consisting of sodium methoxide, sodium ethoxide, sodium tert-butoxide, triethylamine, tri-n-butylamine, tripropylamine and pyridine.

8. A compound represented by formula II or its hydrochloride salt:

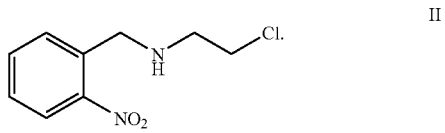

9. A process for preparing a compound represented by formula A by using the compound represented by formula II according to claim 8

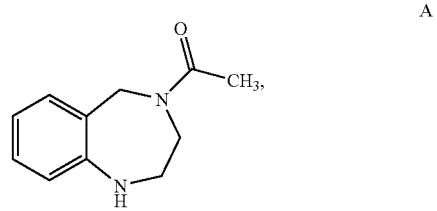

comprising:
acetylating the compound represented by formula II with an acetylating agent selected from the group consisting of Ac$_2$O and acetyl chloride in an organic solvent to give a compound represented by formula IV, and then reducing and cyclizing the compound represented by formula IV in the presence of a reducing agent selected from the group consisting of Fe powder, Zn powder and SnCl$_2$ in an organic solvent to give the compound represented by formula A, which is illustrated by reaction scheme 5:

Reaction scheme 5

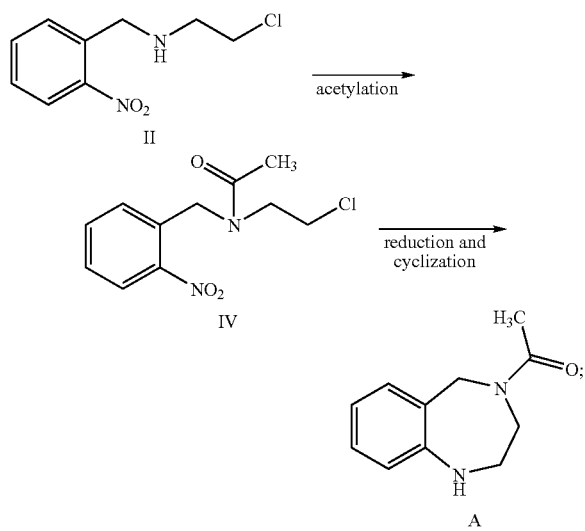

or reducing and cyclizing the compound represented by formula II in the presence of a reducing agent selected from the group consisting of Fe powder, Zn powder and SnCl$_2$ in an organic solvent to give the compound represented by formula III, and then acetylating the compound represented by formula III with an acetylating agent selected from the group consisting of Ac$_2$O and acetyl chloride to give the compound represented by formula A, which is illustrated by reaction scheme 6:

Reaction scheme 6

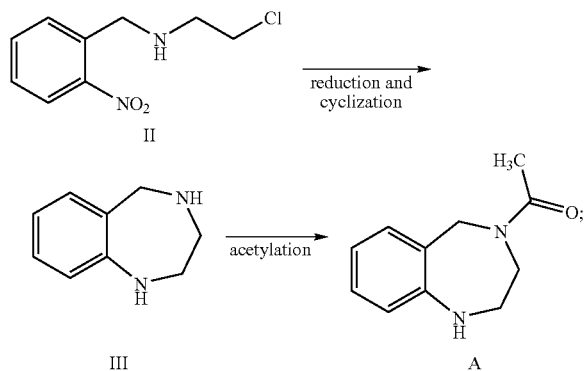

or reducing, cyclizing and acetylating simultaneously the compound represented by formula II in the presence of a reducing agent selected from the group consisting of Fe powder, Zn powder and SnCl$_2$ and an acetylating agent selected from the group consisting of Ac$_2$O and acetyl chloride in an organic solvent to give the compound represented by formula A, as illustrated by reaction scheme 7:

Reaction scheme 7

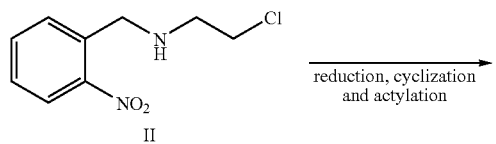

-continued

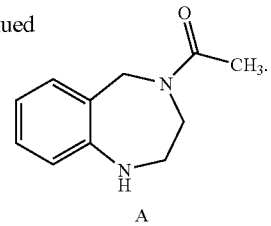

10. The process according to claim 9, wherein the acetylating reaction is performed in the presence of a base selected from the group consisting of sodium methoxide, sodium ethoxide, sodium tert-butoxide, triethylamine, tri-n-butylamine, tripropylamine and pyridine.

11. The process according to claim 9, wherein the organic solvent is one selected from the group consisting of methanol, ethanol, propanol, isopropanol, 1-butanol, 2-butanol, tert-butanol, 1-pentanol, 3-pentanol, ethyl acetate, ethylene glycol diethyl ether, ethylene glycol monomethyl ether, dichloromethane, 1,2-dichloroethane, toluene, xylene, DMF, DMSO, acetonitrile, tetrahydrofuran, dioxane and any mixture thereof.

12. A process for preparing the compound represented by formula A from 2-nitrobenzaldehyde, comprising: in an organic solvent, after condensing 2-nitrobenzaldehyde with 2-chloroethylamine hydrochloride, performing nitro-reduction and cyclization reaction in the presence of a reducing agent selected from the group consisting of Fe powder, Zn powder and SnCl$_2$, followed by a double bond-reduction in the presence of a reducing agent selected from the group consisting of NaBH$_4$, KBH$_4$ and LiBH$_4$ to give the compound represented by formula III; and then acetylating the compound represented by formula III with an acetylating agent to give the compound of formula A; which is illustrated in reaction scheme 8:

Reaction scheme 8

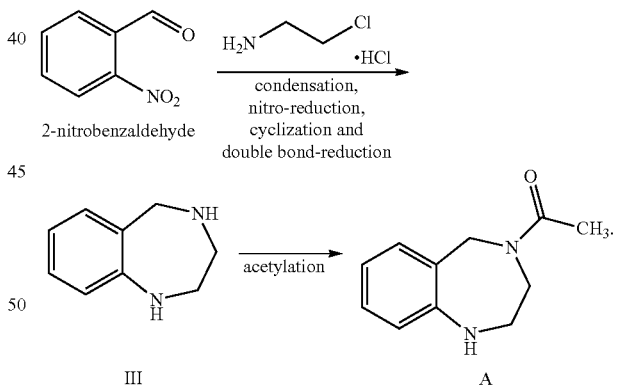

13. A compound represented by formula IV:

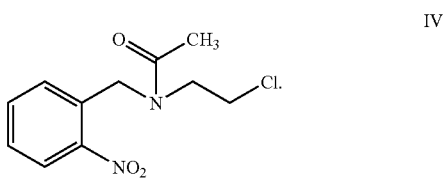

* * * * *